United States Patent
Gershanov et al.

[11] 3,946,086
[45] Mar. 23, 1976

[54] METHOD OF PRODUCING 2,6-DIALKYL- AND 2,6-DIARALKYL-SUBSTITUTED DERIVATIVES OF P-CRESOL

[76] Inventors: Felix Borisovich Gershanov, prospekt Lenina, 81, kv. 6; Alexandr Grigorievich Liakumovich, prospekt Lenina, 23, kv. 4; Jury Ivanovich Michurov, ulitsa Khudaiberdina, 125, kv. 36; Boris Izrailevich Pantukh, ulitsa Khudaiberdina, 130, kv. 115; Grigory Iosifovich Rutman, ulitsa Revoljutsionnaya, 7, kv. 6, all of Sterlitamak; Valerian Mikhailovich Sobolev, Naberezhnaya Maxima Gorkogo, 46/50, kv. 185, Moscow; Alexandr Afroimovich Grinberg, Nagatinskoe shosse, 21, kv. 60, Moscow; Yakov Abramovich Gurvich, Tsentr, Sretensky bulvar, 6, kv. 61, Moscow; Nina Vasilievna Zakharova, prospekt Lenina, 23, kv. 4; Almira Mudarisovna Nafikova, ulitsa Elevatornava, 112, kv. 31, both of Sterlitamak, all of U.S.S.R.

[22] Filed: Oct. 28, 1970

[21] Appl. No.: 84,934

[52] U.S. Cl. .... 260/624 R; 260/621 M; 260/621 H; 260/619 R
[51] Int. Cl.² .......................................... C07C 39/02
[58] Field of Search ............ 260/624 R, 624 C, 624, 260/621 R, 621 H, 621 M

[56] References Cited
UNITED STATES PATENTS

| | | | |
|---|---|---|---|
| 2,841,623 | 7/1958 | Norton et al. | 260/624 R |
| 3,006,969 | 10/1961 | Koetiz | 260/624 R |
| 3,075,832 | 1/1963 | Ecke et al. | 260/624 C |
| 3,367,981 | 2/1968 | Napolitino | 260/624 R |
| 3,592,951 | 7/1971 | Zoveski | 260/624 R |

Primary Examiner—James O. Thomas, Jr.
Assistant Examiner—W. B. Lone
Attorney, Agent, or Firm—Haseltine, Lake & Waters

[57] ABSTRACT

A method of producing 2,6-dialkyl- and 2,6-diaralkyl-substituted derivatives of p-cresol of the general formula

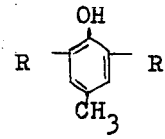

wherein R signifies an alkyl group having from 4 to 12 carbon atoms or

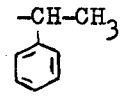

comprising subjecting phenol to alkylation with olefines having from 4 to 12 carbon atoms or with styrene at a temperature of 50°–150°C in the presence of a catalyst, namely, aluminum, taken in an amount of 0.1–5 wt.% of phenol. 2,6-Dialkyl phenol or 2,6-diaralkyl phenol resulting after from the alkylation is treated with a mixture of formaldehyde and dimethylamine or with a product of their interaction having the formula

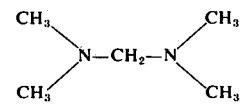

at a temperature of 20°–100°C with subsequent catalytic hydrogenolysis of N,N-dimethyl(3,5-dialkyl-4-hydroxybenzyl)/amine or N,N-dimethyl(3,5-diaralkyl-4-hydroxybenzyl/amine at a temperature of 80°–200°C., molar ratio of hydrogen to the product being treated of 1–5:1 and space velocity of 0.1–2 hour⁻¹.

The products produced by said method feature a high degree of purity, and they can be employed as effective inhibitors of thermooxidation degradation of polymers and hydrocarbon fuels, and also as intermediates for producing p-cresol, and 2-alkyl- and 2-aralkyl-substituted derivatives of p-cresol.

18 Claims, No Drawings

METHOD OF PRODUCING 2,6-DIALKYL- AND 2,6-DIARALKYL-SUBSTITUTED DERIVATIVES OF P-CRESOL

The present invention relates to methods of producing 2,6-dialkyl- and 2,6-diaralkyl-substituted derivatives of p-cresol of the general formula

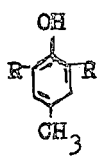

where R signifies an alkyl group having from 4 to 12 carbon atoms or

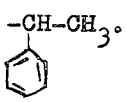

Said products are used as effective inhibitors of thermooxidation degradation of polymers and hydrocarbon fuels, and also as intermediates for producing p-cresol, and 2-alkyl- and 2-aralkyl-substituted derivatives of p-cresol.

Known in the art are methods of producing compounds of the above-stated general formula by alkylating p-cresol with olefines having from 4 to 12 carbon atoms or with styrene at a temperature of 20°–160°C. in the presence of an acid catalyst, such as a cation-exchange resin (cf. an article by V. I. Isagouliantz et al. published in "Prikladnaya Khimiya" ("Applied Chemistry"), 31, 693,1961; U.S. Pat. No. 2,265,582; British Pat. No. 589,070).

The known methods are disadvantageous in that p-cresol required for their realization is a costly and critical product. Thus, for example, the producing of p-cresol from coal-tar fails to meet the needs of industry for this product, since the content of p-cresol in coal-tar proves to be low. Moreover, the now-existing petrochemical methods of producing p-cresol from toluene and phenol do not feature adequate selectivity, which results in a low yield of the product, the very product containing a rather high amount of impurities. Therefore alkyl- and aralkyl-substituted derivatives of p-cresol thus produced also feature a low degree of purity.

The object of the present invention is to make possible the use of an easily available stock in a method of producing 2,6-dialkyl- and 2,6-diaralkyl-substituted derivatives of p-cresol of the above-stated general formula, according to which an aromatic alcohol is alkylated with olefins having from 4 to 12 carbon atoms or with styrene at a temperature of 50°–150°C. in the presence of a catalyst.

In accordance with the said and other objects the present invention resides in using phenol as an aromatic alcohol and aluminum as a catalyst, the latter being taken in an amount of 0.1–5% by weight of phenol, 2,6-dialkyl phenol or 2,6-diaralkyl phenol resulting after the alkylation being treated with a mixture of formaldehyde with dimethylamine or with a product of their interaction of the formula

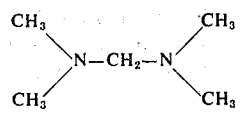

at a temperature of 20°–100°C. with subsequent catalytic hydrogenolysis of N,N-dimethyl-(3,5-dialkyl-4-hydroxybenzyl)amine or N,N-dimethyl-(3,5-diaralkyl-4-hydroxybenzyl)amine at a temperature of 80°–200°C., at a molar ratio of hydrogen to the product being treated of 1–5:1 and a space velocity of 0.1–2 hr$^{-1}$.

By the said method 2,6-dialkyl- and 2,6-diaralkyl-substituted derivatives of p-cresol of the above-stated general formula can be produced from cheap petrochemicals. Moreover, the desired products feature a high degree of purity, since all the stages of the process proceed without the formation of side products.

It is recommended that the treatment of 2,6-dialkyl phenol or 2,6-diaralkyl phenol with a mixture of formaldehyde and dimethylamine or with the product of their interaction having the above-specified formula should be effected at a temperature of 50°–80°C.

It is expedient that the process of hydrogenolysis should be carried out at a temperature of 120°–140°C.

From among the known hydrogenolysis catalysts it is recommended to use nickel-chromium catalyst, nickel-copper catalyst, and, especially, alloyed nickel-aluminum-titanium catalyst, comprising 20–60 wt.% of nickel, 20–40 wt.% of aluminum, 1–10 wt.% of titanium. Said nickel-containing catalysts are most active at comparatively low temperatures, and the last of the cited catalysts proves to be of maximum longevity.

For reducing the required reaction volume and, hence, the volume of the reactor, it is recommended that alkylation be carried out at a pressure of 2–50 abs. atm., preferably, of 3–15 abs. atm.

To accelerate the process of treating 2,6-dialkyl phenol or 2,6-diaralkyl phenol with the mixture of formaldehyde and dimethylamine or with the product of their interaction, said process is recommended to be effected in the medium of saturated aliphatic alcohols, preferably in the medium of monobasic aliphatic alcohols having from 1 to 4 carbon atoms.

For ensuring stable conditions of the catalyst operation, it is recommended that the hydrogenolysis be carried out in the medium of a non-polar organic solvent, preferably in the medium of paraffin or cyclopar-affin hydrocarbons having from 5 to 20 carbon atoms.

The present method of producing 2,6-dialkyl- and 2,6-diaralkyl-substituted derivatives of p-cresol of the above-stated general formula is effected as follows.

Phenol is alkylated with olefins having from 4 to 12 carbon atoms or with styrene at a temperature of 50°–150°C., preferably 100°–110°C., in the presence of a catalyst, namely, aluminum taken in an amount of 0.1–5% by weight of phenol. The olefins may be bubbled through a layer of molten phenol, or the alkylation may be effected with the olefins or styrene being fully dissolved in phenol (a homogeneous medium). In both cases, the process can be carried out either in a flow reactor, or in an autoclave. For diminishing the volume of the reaction apparatus, it is expedient that alkylation should be carried out at a pressure of 2–50 abs. atm., preferably, of 3–15 abs. atm.

The 2,6-dialkyl phenol or 2,6-diaralkyl phenol resulting after the alkylation is treated with a mixture of formaldehyde and dimethylamine or with the product of their interaction which has the above-stated formula, at a temperature of 20°–100°C., preferably at 50°–80°C. The process is expedient to be effected with intense stirring. Said product of interaction of formaldehyde with dimethylamine, prior to treating substituted derivatives of phenol therewith, is obtained by conventional methods such as reacting formaldehyde with dimethylamine at a temperature of 100°–120°C. To speed-up the process of interaction of 2,6-dialkyl phenol or 2,6-diaralkyl phenol with the mixture of formaldehyde and dimethylamine or with the product of their interaction, it is expedient that said process should be carried out in the medium of saturated aliphatic alcohols, preferably in the medium of monobasic aliphatic alcohols having from 1 to 4 carbon atoms.

The resulting N,N-dimethyl(3,5-dialkyl-4-hydroxybenzyl)amine or N,N-dimethyl(3,5-diaralkyl-4-hydroxybenzyl)amine is subjected to catalytic hydrogenolysis in flow reactors at a temperature of 80°–200°C., preferably of 120°–140°C., the molar ratio of hydrogen to the product being treated being 1–5:1 and space velocity 0.1–2 hr$^{-1}$. In the process of hydrogenolysis use may be made either of pure hydrogen, or of hydrogen-containing gases, such as a methane-hydrogen mixture or a nitrogen-hydrogen mixture. As hydrogenolysis catalysts use is made of catalysts that are conventional for this process, such as nickel, palladium, platinum, copper. In view of the reasons stated hereinabove, it proves most expedient to use a nickel-chromium catalyst, nickel-copper catalyst and, especially, alloyed nickel-aluminum-titanium catalyst, comprising 20–60 wt.% of nickel, 20–40 wt.% of aluminum and 1–10 wt.% of titanium.

To ensure stable conditions for the catalyst operation, it is recommended that the process of hydrogenolysis be carried out in the medium of a non-polar organic solvent, preferably in the medium of paraffin or cycloparaffin hydrocarbons having from 5 to 20 carbon atoms.

For a better understanding of the present invention, given hereinbelow are examples which illustrate the production of 2,6-dialkyl- and 2,6-diaralkyl-substituted derivatives of p-cresol.

EXAMPLE 1

1.96 g (0.07 mole) of metallic granulated aluminum was dissolved in 400 g (4.25 mole) of phenol at a temperature of 160°C. Then at a temperature of 110°C. 1000 g (17.86 mole) of isobutylene was passed through the solution over a period of 6 hours. 874.59 g of alkylate were obtained with the following composition as determined chromatographically (in mole percent): phenol, 0.78; tert. butyl phenol, 11.60; 2,6-ditert. butyl phenol, 70.60; 2,4-ditert. butyl phenol, 3.56; 2,4,6-tritert. butyl phenol, 13.46.

The obtained 2,6-ditert. butyl phenol was isolated from the reaction mixture by rectification and treated with the product of interaction of formaldehyde with dimethylamine. Said product of interaction was obtained preliminarily by heating together 100 g of 33% aqueous solution of formaldehyde and 300 g of 33% aqueous solution of dimethylamine at a temperature of 120°C. 122.4 g of the product were obtained. The treatment of 2,6-ditert. butyl phenol with the product thus obtained was effected as follows.

To 206 g of 2,6-ditert.butyl phenol there were added 122.4 g of the product of interaction of formaldehyde with dimethylamine and 350 ml. of methyl alcohol. The mixture was heated to 80°C. and kept at this temperature for 3 hours. The yield was 255.11 g (97% of theory) of N,N-dimethyl(3,5-ditert. butyl-4-hydroxybenzyl)amine, 20.7 g of dimethylamine, 6.9 g of formaldehyde and 6.18 g of 2,6-ditert. butyl phenol. N,N-Dimethyl(3,5-ditert. butyl-4-hydroxybenzyl)amine was isolated from the reaction mixture by recrystallization.

A hydrogenolysis reactor containing nickel-copper catalyst comprising 60 wt.% of nickel and 40 wt.% of copper was charged with 83.3 g of 30% solution of N,N-dimethyl-(3,5-ditert. butyl-4-hydroxybenzyl)amine in decalin, said solution being charged onto said catalyst. Hydrogen was continuously passed through the reactor. The process was carried out at a temperature of 140°C., molar ratio of hydrogen to the product of 1:1 and space velocity of 0.5 hr$^{-1}$. From the resulting catalyst the solvent was distilled off under a vacuum (the residual pressure being 5 mm. Hg) at a temperature of 51°–62°C. The distillation residue of 2,6-ditert. butyl-4-methyl phenol was recrystallized from ethyl alcohol. The yield was 20.4 g of 2,6-ditert. butyl-4-methyl phenol, m.p. 69.6°–69.8°C. Chromatographic analysis showed that there were no admixtures in the obtained product.

EXAMPLE 2

1 g (0.04 mole) of metallic granulated aluminum was dissolved in 400 g (4.25 mole) of phenol at a temperature of 160°C. Then 1150 g (17.86 mole) of isoamylene was passed through the solution over a period of 5 hours at a temperature of 130°C. and pressure of 3 abs. atm. 904 g of alkylate were obtained with the following composition as determined chromatographically (in mole percent): phenol, 1; o-tert. amyl phenol, 10; 2,6-ditert. amyl phenol, 70; 2,4-ditert. butyl phenol, 3; 2,4,6-tritert. amyl phenol, 16.

The obtained 2,6-ditert. amyl phenol was isolated from the reaction mixture by rectification and treated with a mixture of formaldehyde and dimethylamine in the following way. First 87.3 ml of a 33% aqueous solution of formaldehyde were mixed with 220 ml of ethyl alcohol. Into the resulting mixture were introduced 176.6 ml of a 33% aqueous solution of dimethylamine and 220 ml of ethyl alcohol, and then a solution of 236 g of 2,6-ditert. amyl phenol in 700 ml of ethyl alcohol. The mixture thus obtained was heated to 60°C. and kept at this temperature for 4 hours. Then N,N-dimethyl(3,5-ditert. amyl-4-oxybenzyl/amine was crystallized from the reaction mixture. The weight of the crude product was 385 g. This product was then recrystallized in n-heptane. The weight of a refined product was 270 g, this corresponding to the yield equal to 90% of theory.

A flow reactor was filled with alloyed nickel-aluminum-titanium catalyst comprising 40 wt.% of nickel, 55 wt.% of aluminum and 5 wt.% of titanium. Then the reactor was charged with 29.g of N,N-dimethyl(3,5-ditert. amyl-4-hydroxybenzyl)amine dissolved in 70 g of n-decane. A nitrogen-hydrogen mixture containing 60 percent by volume of hydrogen was continuously passed through the reactor. The process of hydrogenolysis was carried out at a temperature of 150°C., molar ratio of hydrogen to the product being processed of 4:1 and space velocity of 1 hr$^{-1}$. From the resulting catalysate the solvent was distilled off as described in Example 1. The distillation residue of 2,6-ditert. amyl-4-methyl phenol was recrystallized from ethyl alcohol. 23.3 g of the target product was obtained, the yield amounting to 97% of theory. The chromatographic analysis showed the absence of any impurities in the product.

EXAMPLE 3

5 g (0.15 mole) of metallic granulated aluminum was dissolved in 400 g (4.25 mole) of phenol at a temperature of 160°C. Then at a temperature of 145°C. 1872 g (18 moles) of styrene were added to the resulting solution.

The mixture was stirred at said temperature over a period of 10 hours. 1740 g of alkylate was obtained comprising 65 mole % of 2,6-di-α-methyl benzyl phenol.

The obtained 2,6-di-α-methyl benzyl phenol was isolated from the reaction mixture by fractional crystallization and treated with a mixture of formaldehyde and dimethylamine in the following manner. A reactor equipped with a stirrer was charged with 302 g of 2,6-di-α-methyl benzyl phenol, and 100 ml of a 33% aqueous solution of formaldehyde and 100 ml of a 33% aqueous solution of dimethylamine were added thereinto. The resulting mixture was heated with intense stirring up to a temperature of 70°C during a period of 6 hours. Then the reaction mixture was cooled, the aqueous layer was separated in a funnel from the oily one, and N,N-dimethyl(3,5-di-α-methylbenzyl-4-hydroxybenzyl)amine was crystallized from the oily layer in an amount of 330 g.

A reactor filled with granulated palladium was charged with 330 g of N,N-dimethyl(3,5-di-α-methyl-benzyl-4-hydroxybenzyl)amine. A methane-hydrogen mixture containing 90 per. cent by volume of hydrogen was continuously passed through the reactor. The process of hydrogenolysis was carried out at a temperature of 190°C, molar ratio of hydrogen to the product being processed of 5:1 and space velocity of 0.1 hr$^{-1}$. 270 g of 2,6-di-α-methyl benzene-4-methyl phenol was obtained, the yield being 89% of theory. Chromatographic analysis showed that there were no admixtures in the product obtained.

Though the present invention has been described in connection with its preferred embodiment, it is understood, that various changes and modifications may be made by those skilled in the art without departing from the spirit and scope of the invention. These changes and modifications are to be considered as falling within the spirit and scope of the invention as stated by the following claims.

What is claimed is:

1. A method of producing a 2,6-dialkyl-p-cresol of the formula

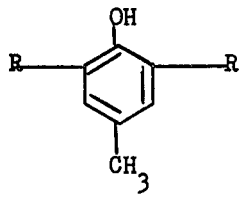

wherein R signifies an alkyl radical having from 4 to 12 carbon atoms comprising alkylating phenol with an olefin having from 4 to 12 carbon atoms at a temperature of 50°–150°C. in the presence of aluminum as a catalyst in an amount of 0.1–5% by weight of the phenol to form an alkylated phenol, treating said alkylated phenol with a reactant selected from the group consisting of (a) a mixture of formaldehyde and dimethylamine and (b) their interaction product having the formula

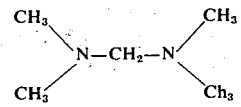

at a temperature of 20°–100°C. to form an intermediate product, N,N-dimethyl-3,5-dialkyl-4-hydroxy benzylamine, and subjecting said intermediate product to catalytic hydrogenolysis at 80°–200°C. using a molar ratio of hydrogen to said intermediate product of 1–5:1 and a space velocity of 0.1–2 hour$^{-1}$ to form the 2,6-dialkyl-p-cresol.

2. A method as claimed in claim 1, wherein alkylation is carried out at a pressure of 2–50 abs. atm.

3. A method as claimed in claim 2, wherein alkylation is carried out at a pressure of 3–15 abs. atm.

4. A method of producing a 2,6-dialkyl-p-cresol of the formula

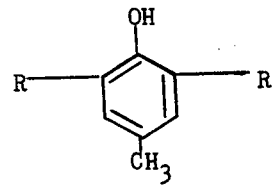

wherein R signifies an alkyl radical having from 4 to 12 carbon atoms comprising (1) reacting the corresponding 2,6-dialkyl phenol with a reagent selected from the group consisting of (a) a mixture of formaldehyde and dimethyl-amine and (b) their interaction product having the formula

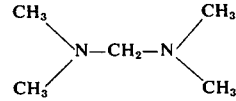

at a temperature of 20°–100°C. to form an intermediate product N,N-dimethyl-3,5-dialkyl-4-hydroxybenzylamine and (2) subjecting said intermediate product to catalytic hydrogenolysis at 80°–200°C. using a molar ratio of hydrogen to said intermediate product of 1–5:1 and a space velocity of 0.1–2 hour$^{-1}$ to form the 2,6-dialkyl-p-cresol.

5. A method as claimed in claim 4, wherein the treatment of 2,6-dialkyl phenol with the mixture of formaldehyde and dimethyl-amine is carried out at a temperature of 50°–80°C.

6. A method as claimed in claim 4, wherein the treatment of 2,6-dialkyl phenol with the product of interaction of formaldehyde with dimethylamine is carried out at a temperature of 50°–80°C.

7. A method as claimed in claim 4, wherein the treatment of 2,6-dialkyl phenol with the mixture of formaldehyde and dimethylamine is carried out in the medium of saturated aliphatic alcohol.

8. A method as claimed in claim 7, wherein the monobasic aliphatic alcohol has 1 to 4 carbon atoms.

9. A method as claimed in claim 4, wherein the treatment of 2,6-dialkyl phenol with the product of interaction of formaldehyde with dimethylamine is carried out in the medium of a saturated aliphatic alcohol.

10. A method as claimed in claim 9, wherein the monobasic aliphatic alcohol has 1 to 4 carbon atoms.

11. A method of producing a 2,6-dialkyl-p-cresol which comprises subjecting a N,N-dimethyl-3,5-dialkyl-4-hydroxybenzylamine of the formula

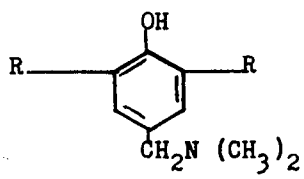

wherein R signifies an alkyl radical having 4 to 12 carbon atoms to catalytic hydrogenolysis at 80°–200°C. using a molar ratio of hydrogen to said N,N-dimethyl-3,5-dialkyl-4-hydroxybenzylamine of 1–5:1 and a space velocity of 0.1–2 hour$^{-1}$ to form the 2,6-dialkyl-p-cresol.

12. A method as claimed in claim 11, wherein hydrogenolysis is effected at a temperature of 120°–140°C.

13. A method as claimed in claim 11, wherein nickel-chromium catalyst is used as a hydrogenolysis catalyst.

14. A method as claimed in claim 11, wherein nickel-copper catalyst is used as a hydrogenolysis catalyst.

15. A method as claimed in claim 11, wherein alloyed nickel-aluminum-titanium catalyst comprising 20–60 wt.% of nickel, 20–40 wt.% of aluminum and 1–10 wt.% of titanium is used as a hydrogenolysis catalyst.

16. A method as claimed in claim 11, wherein hydrogenolysis is carried out in the medium of a non-polar organic solvent.

17. A method as claimed in claim 16, wherein the non-polar solvent is a hydrocarbon having from 5 to 20 carbon atoms.

18. A method as claimed in claim 16, wherein the non-polar solvent is a cycloparaffin hydrocarbon having 5 to 20 carbon atoms.

* * * * *